(12) United States Patent
Pirela-Cruz

(10) Patent No.: US 10,383,625 B1
(45) Date of Patent: Aug. 20, 2019

(54) SCAPHOID FIXATION WITH AN ANATOMICALLY DESIGNED STAPLE

(71) Applicant: Miguel Angel Pirela-Cruz, El Paso, TX (US)

(72) Inventor: Miguel Angel Pirela-Cruz, El Paso, TX (US)

( * ) Notice: Subject to any disclaimer, the term of this patent is extended or adjusted under 35 U.S.C. 154(b) by 85 days.

(21) Appl. No.: 15/152,458

(22) Filed: May 11, 2016

Related U.S. Application Data

(60) Provisional application No. 62/187,178, filed on Jun. 30, 2015.

(51) Int. Cl.
*A61B 17/064* (2006.01)
*A61B 17/84* (2006.01)
*A61B 17/68* (2006.01)
*A61B 17/00* (2006.01)

(52) U.S. Cl.
CPC ........ *A61B 17/0642* (2013.01); *A61B 17/846* (2013.01); *A61B 2017/00858* (2013.01); *A61B 2017/681* (2013.01)

(58) Field of Classification Search
CPC .......... A61B 17/064; A61B 2017/0641; A61B 17/0642; A61B 17/809; A61B 17/846
See application file for complete search history.

(56) References Cited

U.S. PATENT DOCUMENTS

| | | | |
|---|---|---|---|
| 5,053,038 A | 10/1991 | Sheehan | |
| 5,246,443 A * | 9/1993 | Mai | A61B 17/0642 606/219 |
| 5,788,698 A * | 8/1998 | Savornin | A61B 17/0642 606/142 |
| 5,947,999 A * | 9/1999 | Groiso | A61B 17/0642 606/216 |
| 6,059,787 A * | 5/2000 | Allen | A61B 17/0642 606/75 |
| 6,187,009 B1 | 2/2001 | Herzog | |
| D586,915 S * | 2/2009 | Grim | D24/145 |
| 8,062,297 B2 * | 11/2011 | Faillace | A61B 17/0642 606/75 |
| D691,720 S * | 10/2013 | Cheney | D24/145 |
| 2005/0096660 A1 | 5/2005 | Allen | |
| 2008/0306480 A1 | 12/2008 | Wilson | |
| 2010/0023062 A1 | 1/2010 | Faillace | |
| 2010/0125275 A1 | 5/2010 | Kinmon | |
| 2013/0184768 A1 | 7/2013 | McIff | |
| 2014/0018809 A1 | 1/2014 | Allen | |
| 2014/0277516 A1 | 9/2014 | Miller | |
| 2015/0133940 A1 | 5/2015 | Palmer | |
| 2015/0230839 A1 * | 8/2015 | Riccione | A61B 17/8014 606/297 |

FOREIGN PATENT DOCUMENTS

FR    3023468 A1 *  1/2016  ......... A61B 17/0684

* cited by examiner

*Primary Examiner* — Christian A Sevilla
(74) *Attorney, Agent, or Firm* — Plager Schack LLP; Marl H. Plager; Michael J. O'Brien

(57) ABSTRACT

A fixation for a mid-waist fracture of a scaphoid bone includes a top portion joined to two prongs. The top portion is bent to match a lateral curvature and an anteroposterior curvature of the scaphoid bone. A plurality of spikes are installed on the two prongs. When one inserts the fixation into the scaphoid bone, the plurality of spikes hold the fixation in place.

6 Claims, 7 Drawing Sheets

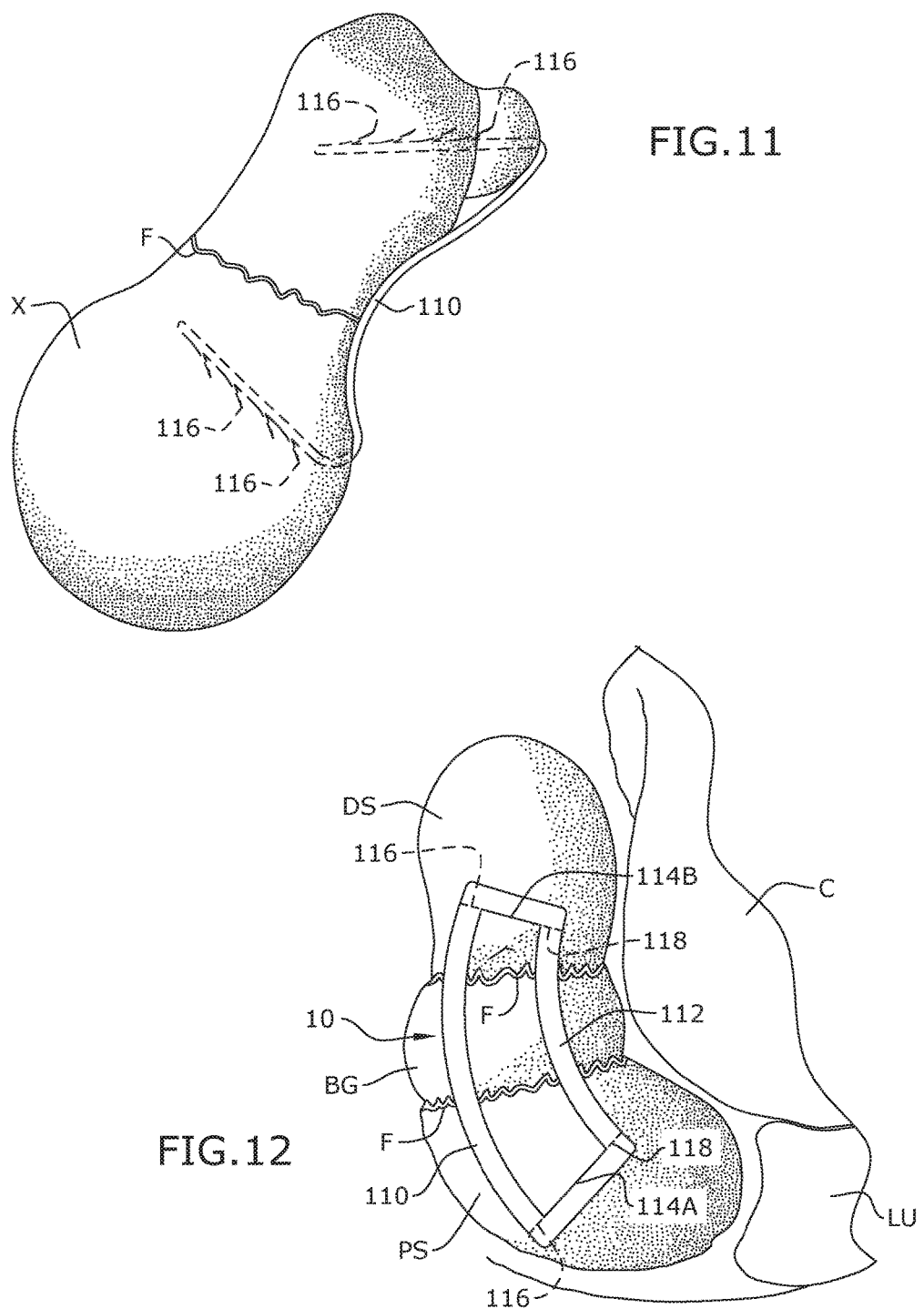

SCAPHOID FIXATION WITH AN ANATOMICALLY DESIGNED STAPLE

RELATED APPLICATION

This application claims priority to provisional patent application U.S. Ser. No. 62/187,178 filed on Jun. 30, 2015, the entire contents of which is herein incorporated by reference.

BACKGROUND

The embodiments herein relate generally to equipment that helps in healing a scaphoid fracture of the wrist.

The scaphoid is one of eight small bones that make up the "carpal bones" of the wrist. It connects two rows of these bones—the proximal row (closer to the forearm) and the distal row (closer to the hand). This connection puts it at extra risk for injury. A fracture of the scaphoid bone usually occurs from a fall onto the outstretched hand.

If the fracture is non-displaced (that is, the bone has not moved out of place at the fracture), it usually can be successfully treated with a cast. Although the fracture may heal in as little as six weeks, it may take longer for some patients.

If the fracture is in a certain part of the bone or if the fracture is at all displaced (bone ends have shifted), surgery might be the best option. This might include the insertion of a screw or pins. However, it is technically hard to use theses screws and pins and therefore, is more prone to developing complications. Some endeavors in this field include: U.S. Patent Application Pre-grant Publication 2015/0133940 filed by Palmer; U.S. Patent Application Pre-grant Publication 2014/0277516 filed by Miller; U.S. Patent Application Pre-grant Publication 2014/0018809 filed by Allen; and U.S. Pat. No. 5,053,038 issued to Sheehan.

Palmer teaches an elastic bone staple that holds itself into place by compressing a bone. Miller teaches a bone staple with unidirectional barbs to prevent removal. Allen adds some curvature onto Miller's design. None of these teach having the staple manufactured to match a lateral curvature and an anteroposterior curvature of the scaphoid bone. Embodiments of the disclosed invention solve these problems.

SUMMARY

A fixation for a mid-waist fracture of a scaphoid bone includes a top portion joined to two prongs. The top portion is bent to match a lateral curvature and an anteroposterior curvature of the scaphoid bone. A plurality of spikes are installed on the two prongs. When one inserts the fixation into the scaphoid bone, the plurality of spikes hold the fixation in place.

In some embodiments, the fixation is sized such that an equal length of the top portion is to a proximal side of the mid-waist fracture and a distal side of the mid-waist fracture while the top portion is curved. In this regard, at as many points as possible, a forward distance and a rearward distance to edges of the scaphoid bone are approximately equal. The fixation can be shaped to form to a bone graft between a proximal scaphoid and a distal scaphoid. The prongs can have a length that is about two thirds of a thickness of the scaphoid bone at a site of mid-waist fracture.

In some embodiments, the top portion can further comprise a forward top side connected to a proximal top side and distal top side. A rearward side can be attached to a proximal top side and a distal top side.

In some embodiments, the fixation can be shaped to form to a bone graft between a proximal scaphoid and a distal scaphoid.

In some embodiments, the top portion can further comprise a central top side, attached to a forward top side and a rear top side. A central prong can be smoothly connected to the central top side and further comprising a plurality of central side teeth. A forward prong can be smoothly connected to the forward top side and further comprising a plurality of forward side teeth. A rear prong can be smoothly connected to the rear top side and further comprising a plurality of rear side teeth.

BRIEF DESCRIPTION OF THE FIGURES

The detailed description of some embodiments of the invention is made below with reference to the accompanying figures, wherein like numerals represent corresponding parts of the figures.

FIG. 11 is a lateral view of an embodiment of the invention shown in use.

FIG. 12 is a perspective view of the volar side of the left wrist of a nonunions scaphoid bone shown in use.

DETAILED DESCRIPTION OF CERTAIN EMBODIMENTS

Figure 1:
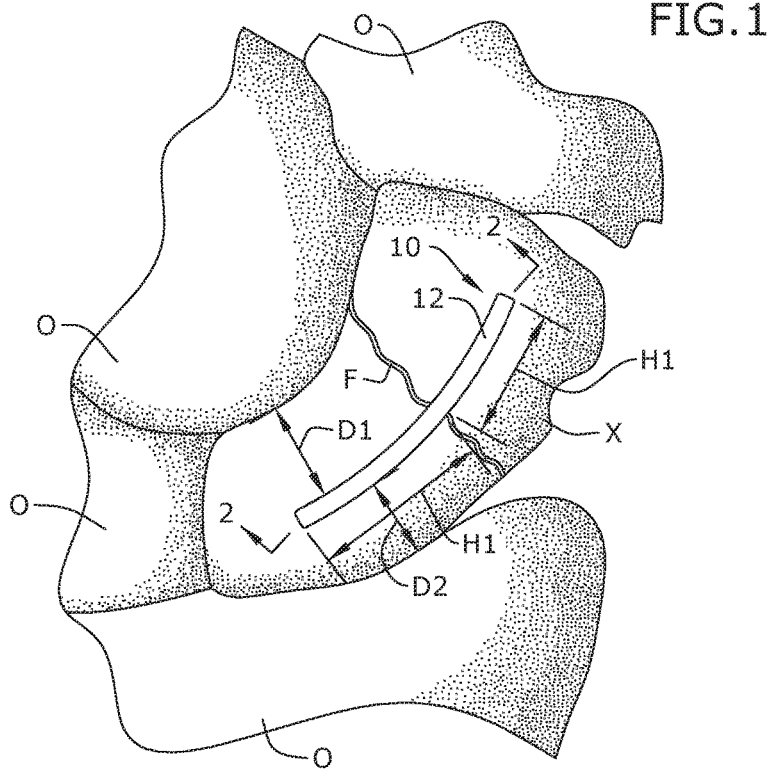
FIG. 1 is a dorsal view of an embodiment of the invention shown in use.
Figure 2:
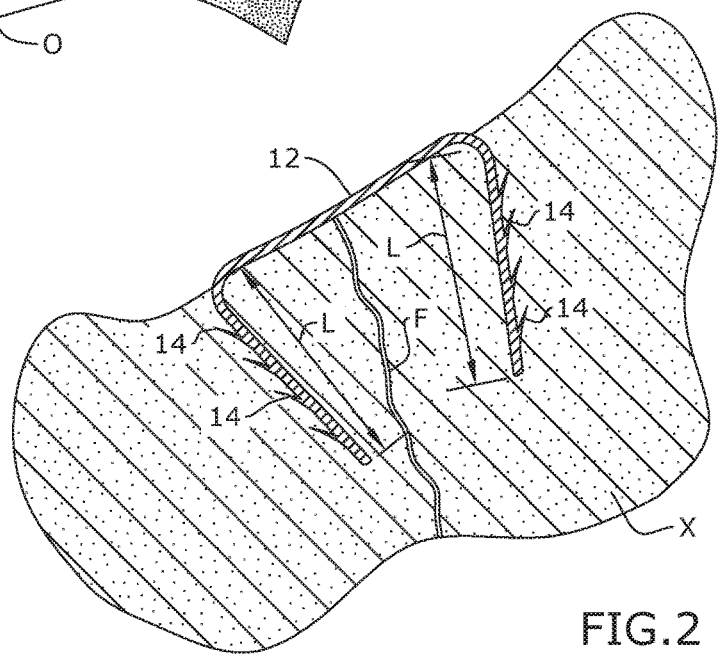
FIG. 2 is a section view of an embodiment of the invention taken from 2-2 in FIG. 1.
Figure 3:
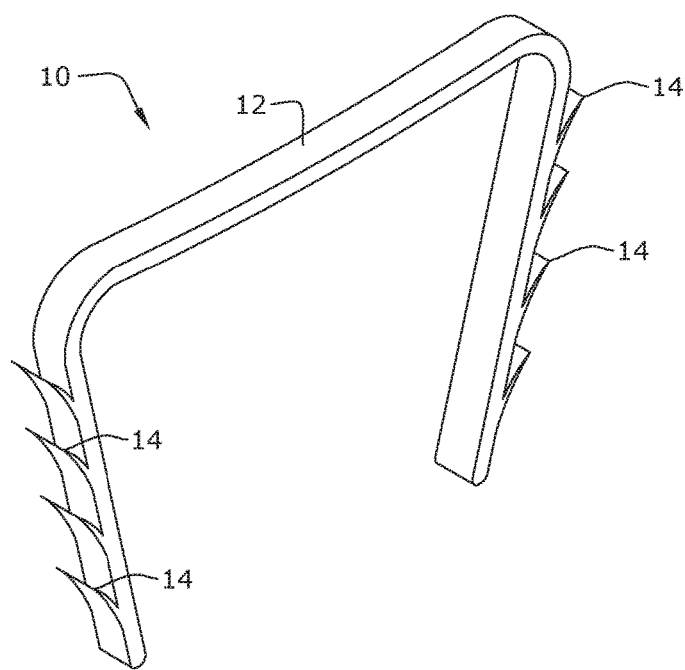
FIG. 3 is a perspective view of an embodiment of the invention.

By way of example, and referring to FIGS. 1-3, scaphoid X is shown with fracture F that is being treated with fixation 10. As noted above, scaphoid X is surrounded by other bones O. Fixation 10 comprises a flat topside parallel to a surface on scaphoid X perpendicular to fracture 14. Note that fixation 10 is anatomically customized to scaphoid X, being bent laterally to a top surface of scaphoid X. There are two prongs shown on fixation 10 that extend downward into scaphoid X. However, in some embodiments there can be more than two prongs. For instance three or more prongs may be necessary depending on the fracture being treated. Each prong has a plurality of spikes 14 that hold fixation 10 into place and prevent involuntary removal. Fixation 10 is sized such that an equal length H1 of a top portion is to a proximal side of fracture F and a distal side of fracture F. At the same time, the top portion 12 is curved, such that, at as many points as possible, a forward distance D1 and a rearward distance D2 are approximately equal.

Fixation 10 has a top portion 12 and prongs which have a length L and width that can be customized to the anatomy of the patient such that L is about two thirds the thickness of scaphoid X at the site of fracture F. However, a few standard sizes could be manufactured as well. There are regulatory requirements for selection of materials for embedded medical devices that should be followed in manufacture. Presently nickel titanium alloys, sometimes called nitinol are proposed, but other compounds may also be effective.

Figure 4:
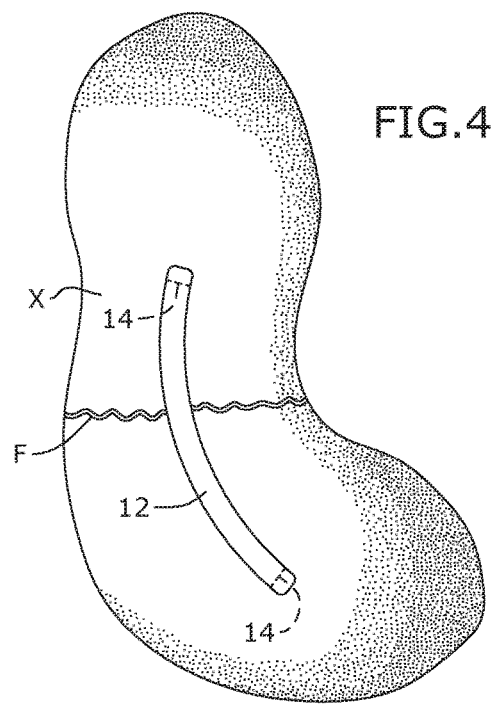
FIG. 4 is an anteroposterior view of an embodiment of the invention illustrating the left scaphoid (volar side) shown in use.
Figure 5:
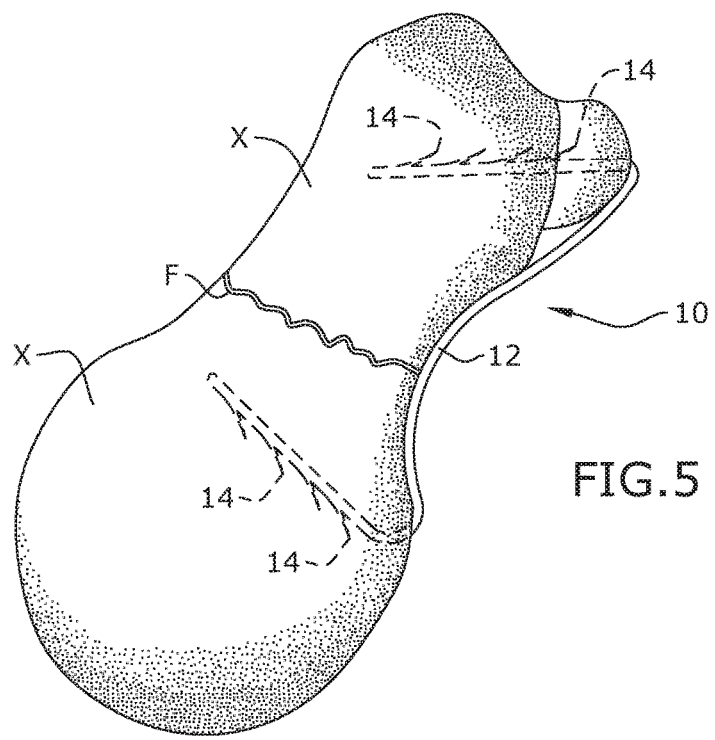
FIG. 5 is a lateral view of an embodiment of the invention shown in use.

Turning to FIG. 4 and FIG. 5, fixation 10 is formed such that it fits along the lateral and anteroposterior curves of scaphoid X. Typically, a user would insert fixation 10 toward the center of scaphoid X where the center of fixation 10 is close to the center of fracture 14. However, those skilled in the art may develop minor deviations from this within the scope of the invention.

Figure 6:
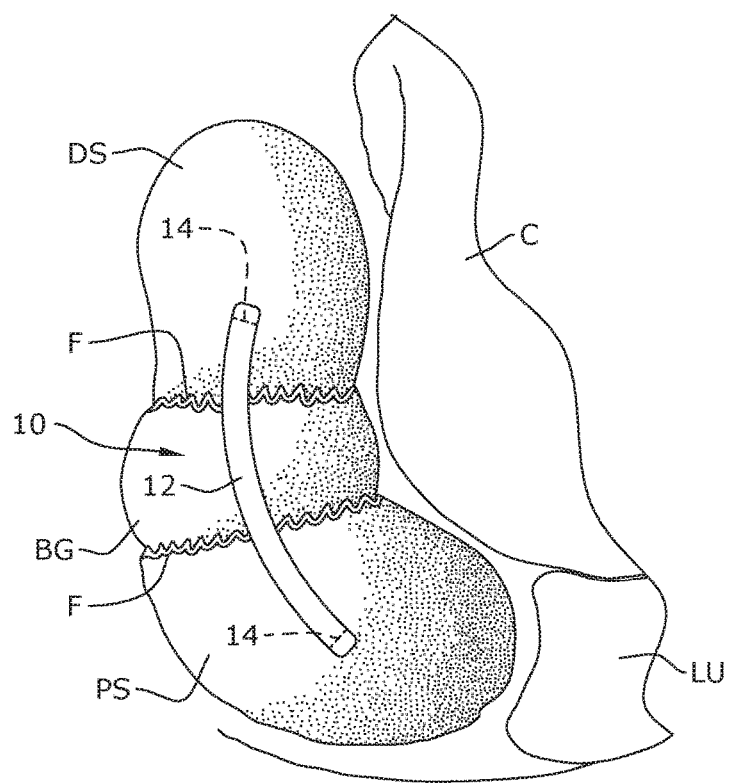
FIG. 6 is a perspective view of the volar side of the left wrist of a nonunions scaphoid bone shown in use.

As shown in FIG. 6, in some cases, there can be a nonunions scaphoid bone X which forms proximal scaphoid PS and distal scaphoid DS that requires bone graft BG. This is shown proximate capitate C and lunate LU. In this is situation fixation 10 straddles bone graft BG across proximal scaphoid PS and distal scaphoid DS. Here, rather than adapting the shape to the nonunions scaphoid bone X, the shape of bone graft BG is also used when forming fixation 10.

Figure 7:
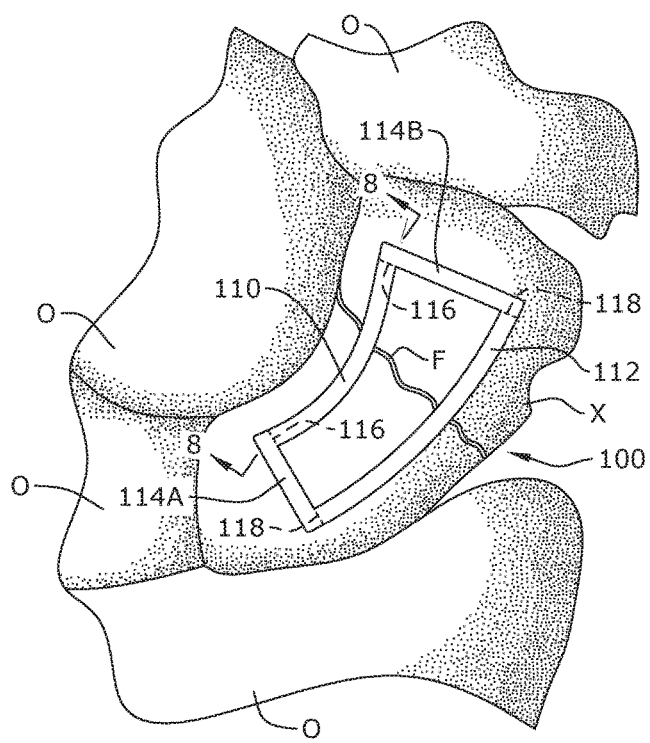
FIG. 7 is a top view of an embodiment of the invention.
Figure 8:
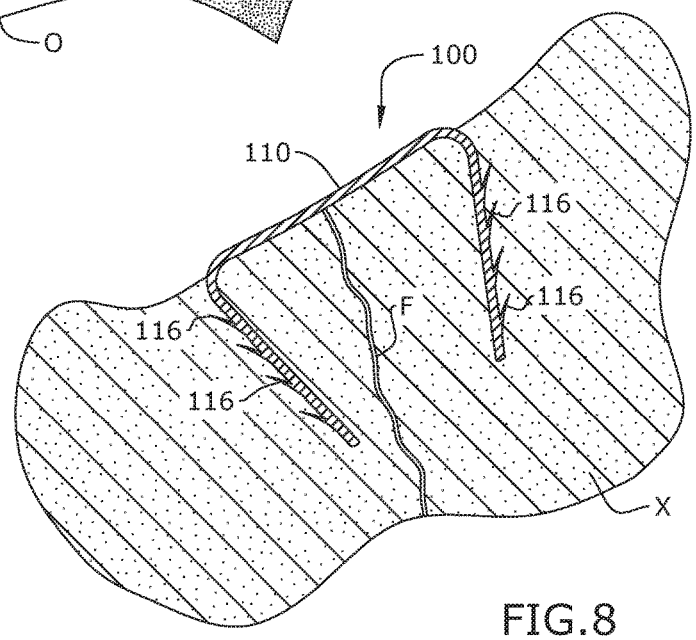
FIG. 8 is a section view of an embodiment of the invention taken from 8-8 in FIG. 7.
Figure 9:
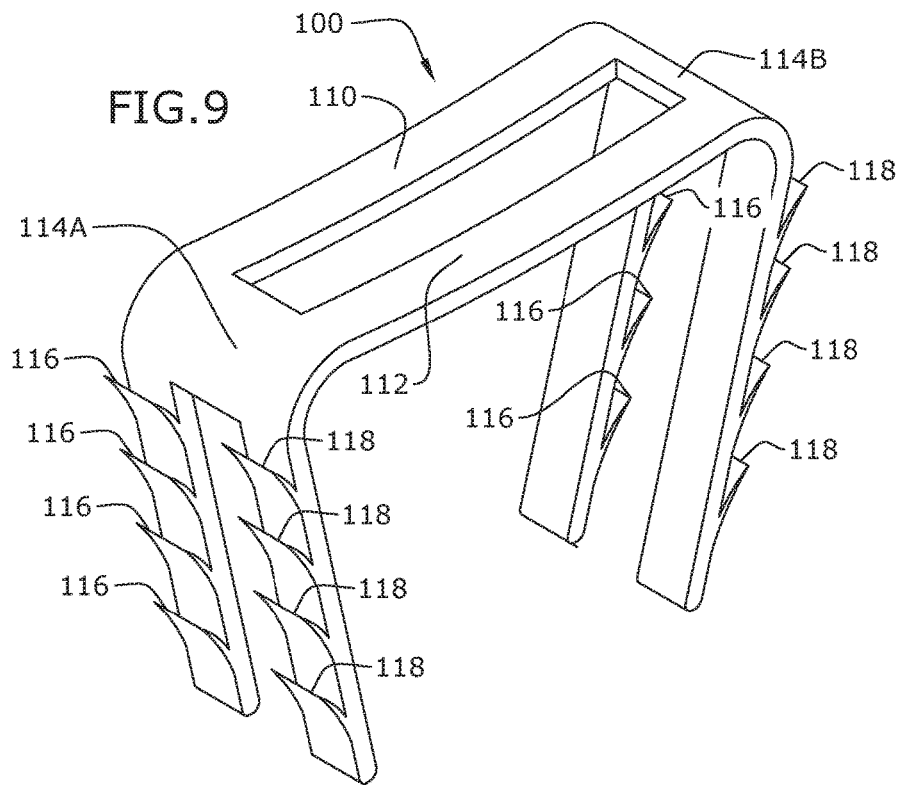
FIG. 9 is a perspective view of an embodiment of the invention.
Figure 10:
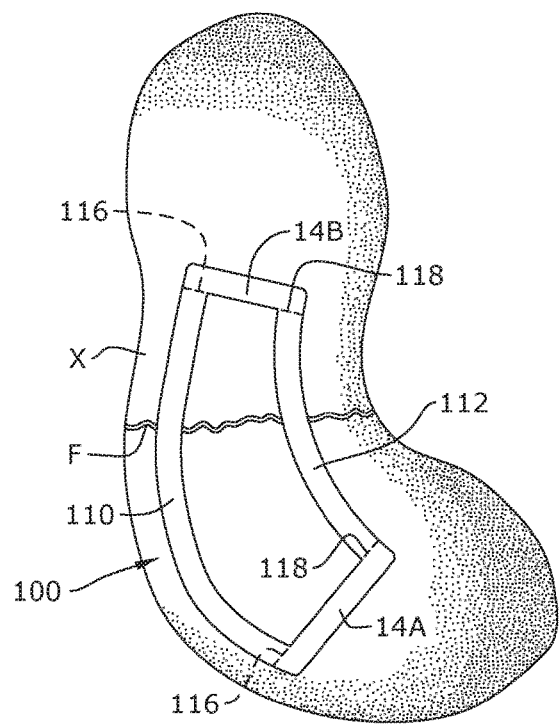
FIG. 10 is an anteroposterior view of an embodiment of the invention illustrating the left scaphoid (volar side) shown in use.

Turning to FIG. 7, scaphoid X is shown with fracture F that is being treated with fixation 110. Fixation 110 further comprises forward top side 110 connected to proximal top side 114A and distal top side 114B. Proximal top side 114A and distal top side 114B are further attached to rearward side 112. The proximal top side 114A smoothly transitions into a forward proximal side further comprising a plurality of forward proximal side teeth 120 and a rearward proximal side further comprising a plurality of rearward proximal side teeth 122.

As shown in FIG. 12, in some cases, there can be a nonunions scaphoid bone X which forms proximal scaphoid PS and distal scaphoid DS that requires bone graft BG. This is shown proximate capitate C and lunate LU. In this is situation fixation 110 straddles bone graft BG across proximal scaphoid PS and distal scaphoid DS. Here, rather than adapting the shape to the nonunions scaphoid bone X, the shape of bone graft BG is also used when forming fixation 110.

Figure 13:
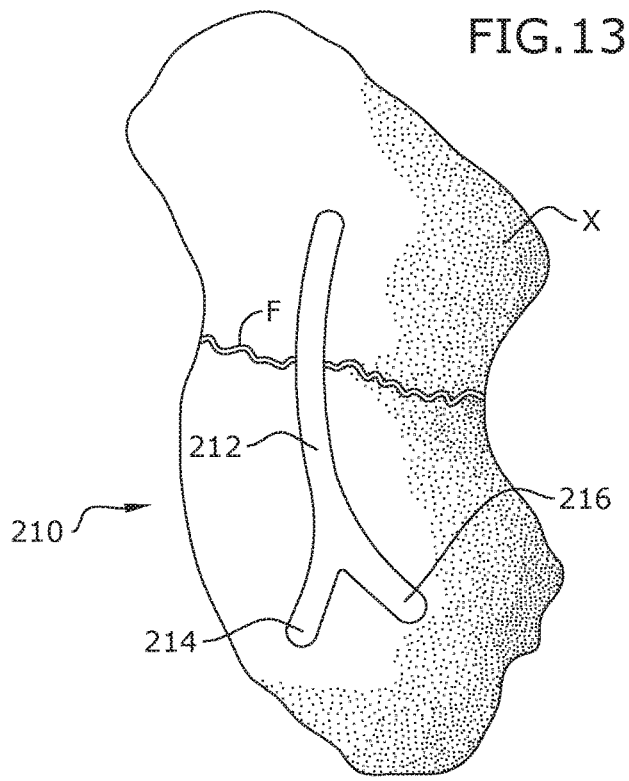
FIG. 13 is a lateral view of an embodiment of the invention shown in use.
Figure 14:
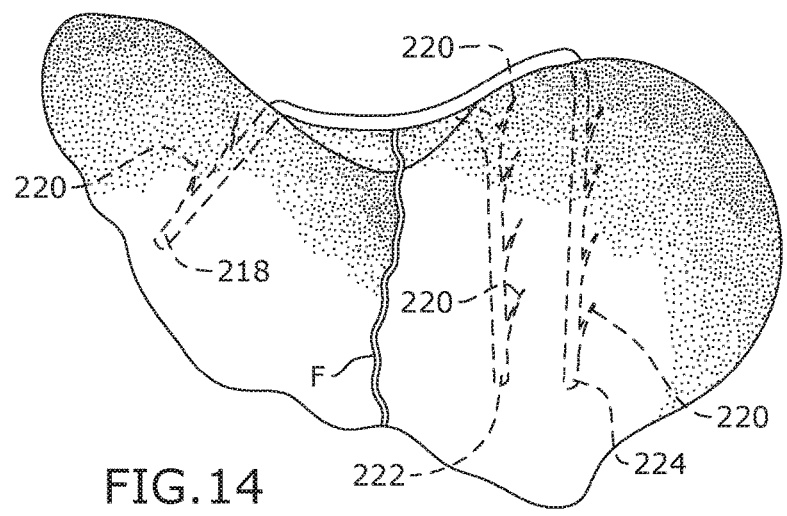
FIG. 14 is a perspective view of the volar side of the left wrist of a nonunions scaphoid bone shown in use.

Turning to FIGS. 13-14, fixation 210 is appropriate where a proximal side of scaphoid bone X is much thicker than a distal side of scaphoid bone X. Here, there is a difficulty in holding the smaller portion together. Fixation 210 solves this with central top side 212 being attached to forward top side 214 and rear top side 216. Central top side 212 is smoothly connected to central prong 218 which further comprises a plurality of central prong teeth 220. Forward top side 214 is smoothly connected to forward prong 224 which further comprises a plurality of forward prong teeth 220. Rear top side 216 is smoothly connected to rear prong 222 which further comprises a plurality of rear prong teeth 220.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A fixation for mid-waist fracture of a scaphoid bone; the fixation comprising:
    a top portion joined to two prongs; wherein the top portion is bent to match a lateral curvature and an anteroposterior curvature of the scaphoid bone; wherein the top portion is bent at a concave shape extending inward towards the scaphoid bone; wherein the top portion further comprises:
    a forward top side connected to a proximal top side and a distal top side and a rearward side, attached to the proximal top side and the distal top side; wherein the forward top side, the proximal top side, the distal top side, and the rearward side are arranged in a quadrilateral to align with the lateral curvature and the anteroposterior curvature of the scaphoid bone; and
    a plurality of spikes, installed on the two prongs; wherein inserting the fixation into the scaphoid bone causes the plurality of spikes to hold the fixation in place.

2. The fixation of claim 1, wherein the fixation is sized such that an equal length of the top portion is to a proximal side of the mid-waist fracture and a distal side of the mid-waist fracture while the top portion is curved, such that, at as many points as possible, a forward distance and a rearward distance to edges of the scaphoid bone are approximately equal.

3. The fixation of claim 2, wherein the fixation is shaped to form to a bone graft between a proximal scaphoid and a distal scaphoid.

4. The fixation of claim 3, wherein the two prongs have a length that is about two thirds of a thickness of the scaphoid bone at a site of mid-waist fracture.

5. The fixation of claim 1, wherein the fixation is shaped to form to a bone graft between a proximal scaphoid and a distal scaphoid.

6. A fixation for mid-waist fracture of a scaphoid bone; the fixation comprising:

a top portion joined to three prongs; wherein the top portion is bent to match a lateral curvature and an anteroposterior curvature of the scaphoid bone; wherein the top portion is bent at a concave shape extending inward towards the scaphoid bone; wherein the top portion further comprises: a forward top side connected to a proximal top side and a distal top side and a rearward side, attached to the proximal top side and the distal top side; wherein the forward top side, the proximal top side, the distal top side, and the rearward side are arranged in a quadrilateral to align with the lateral curvature and the anteroposterior curvature of the scaphoid bone;

a plurality of spikes, installed on the three prongs; wherein inserting the fixation into the scaphoid bone causes the plurality of spikes to hold the fixation in place;

a central top side, attached to the forward top side and the rearward side;

a forward prong, smoothly connected to the forward top side and further comprising a plurality of forward side teeth; and a rear prong, smoothly connected to the rearward side and further comprising a plurality of rear side teeth, wherein one of the three prongs is a central prong, smoothly connected to the central top side and further wherein the plurality of spikes is a plurality of central side teeth, and wherein another of the three prongs is a second forward prong, smoothly connected to the forward top side and further wherein the plurality of spikes is a plurality of forward side teeth.

* * * * *